United States Patent
Doerr

(10) Patent No.: US 9,278,227 B2
(45) Date of Patent: Mar. 8, 2016

(54) IMPLANTABLE DEFIBRILLATION ARRANGEMENT AND ELECTRODE LEAD

(75) Inventor: Thomas Doerr, Berlin (DE)

(73) Assignee: BIOTRONIK SE & CO. KG, Berlin (DE)

(*) Notice: Subject to any disclaimer, the term of this patent is extended or adjusted under 35 U.S.C. 154(b) by 29 days.

(21) Appl. No.: 13/539,412

(22) Filed: Jun. 30, 2012

(65) Prior Publication Data

US 2013/0023945 A1 Jan. 24, 2013

Related U.S. Application Data

(60) Provisional application No. 61/510,082, filed on Jul. 21, 2011.

(51) Int. Cl.
*A61N 1/362* (2006.01)
*A61N 1/39* (2006.01)
*A61N 1/05* (2006.01)

(52) U.S. Cl.
CPC ............ *A61N 1/3918* (2013.01); *A61N 1/0563* (2013.01); *A61N 1/3962* (2013.01)

(58) Field of Classification Search
CPC ............ A61N 1/3962; A61N 1/36128; A61N 1/3956; A61N 1/05; A61N 1/0563; A61N 1/39; A61N 1/3912; A61N 1/39128
USPC ........................................................ 607/5, 7
See application file for complete search history.

(56) References Cited

U.S. PATENT DOCUMENTS

| 5,325,870 A | 7/1994 | Kroll et al. |
| 5,336,253 A | 8/1994 | Gordon et al. |
| 5,545,183 A * | 8/1996 | Altman ................. A61N 1/056 607/4 |
| 6,167,291 A * | 12/2000 | Barajas ............. A61B 5/04286 439/909 |
| 2006/0217772 A1* | 9/2006 | Libbus et al. ..................... 607/9 |
| 2010/0114211 A1* | 5/2010 | Donofrio ............. A61N 1/3718 607/5 |
| 2010/0137929 A1* | 6/2010 | Libbey et al. .................... 607/5 |

FOREIGN PATENT DOCUMENTS

| EP | 2143466 | 1/2010 |
| WO | 00/20071 | 4/2000 |

OTHER PUBLICATIONS

European Search Report, dated Jan. 27, 2014, 6 pages.

* cited by examiner

*Primary Examiner* — Michael Kahelin
*Assistant Examiner* — Minh Duc Pham
(74) *Attorney, Agent, or Firm* — Arc IP Law, PC; Joseph J. Mayo

(57) ABSTRACT

An implantable defibrillation arrangement comprising a defibrillation device having a sensing component and a defibrillation component, and an electrode lead comprising a lead body, a plug, a sensing electrode for sensing cardiac action potentials with a first electrode supply lead, and a defibrillation electrode for transmitting shock pulses to cardiac tissue with a second electrode supply lead, wherein a switching unit is provided to switch the sensing electrode to the potential of the defibrillation electrode in response to the output of a defibrillation shock by the defibrillation component.

9 Claims, 3 Drawing Sheets

IMPLANTABLE DEFIBRILLATION ARRANGEMENT AND ELECTRODE LEAD

This application claims the benefit of U.S. Provisional Patent Application 61/510,082 filed on 21 Jul. 2011, the specification of which is hereby incorporated herein by reference.

BACKGROUND OF THE INVENTION

1. Field of the Invention

At least one embodiment of the invention relates to an implantable defibrillation arrangement.

2. Description of the Related Art

Implantable defibrillators or cardioverters (ICD) have been known and used in clinical applications for a long time, and have been the subject of sustained technical development for decades. This applies to an even greater extent for implantable cardiac pacemakers and the associated electrode leads. Combination cardiac stimulation and defibrillation arrangements, including the electrode leads (ICD electrodes) developed especially therefore, have also become established as a special class of devices on the device market and in clinical applications. Such combination devices are referred to as cardiac pacemakers for cardiac resynchronization therapy with defibrillator, or CRT-D devices.

FIG. 1 shows a schematic depiction of such an arrangement 100 including electrodes implanted in the heart H of a patient. Accordingly, a cardiac stimulation and defibrillation device 110 is connected to the heart H via an electrode lead 120 which comprises three lead branches or electrode supply leads 130, 140 and 150. Each lead branch comprises sensing or stimulation electrodes (which are not depicted individually) on or near the distal end thereof, and lead branch 150 also comprises an elongated defibrillation electrode 160. In the arrangement shown, lead branch 130 is placed in the right atrium, lead branch 140 is placed in the left atrium of the heart H, and lead branch 150 on which defibrillation electrode 160 is installed is placed in the right ventricle (RV).

When a shock is administered, only the shock coil of the RV electrode is switched to a high-voltage potential, while the bipolar sensing and stimulation system remains at the output potential. The supply leads inside electrode lead 120 must therefore be designed with insulating clearances that are resistant to high voltage.

In all of the ICD electrodes known to date, insulating clearances for high voltages must be maintained within the electrode lead, which limits a further reduction of the electrode diameter and prevents the integration of a shock coil onto a CS electrode.

BRIEF SUMMARY OF THE INVENTION

The problem addressed by at least one embodiment of the invention is therefore that of providing an improved implantable defibrillation arrangement which comprises, in particular, an electrode lead which is more easily placed and ensures flexible use in different application situations, thereby enabling same to be utilized with greater ease in broader clinical applications overall.

This problem is solved by a defibrillation arrangement having the features as claimed herein. Advantageous embodiments of the inventive idea are the subject matter of the respective dependent claims.

The objective of at least one embodiment of the invention is to substantially reduce the diameter and increase the flexibility of the electrode lead in an arrangement of the stated type by substantially reducing the required insulation resistances within the lead. To this end, at least one embodiment of the invention makes use of the further idea of substantially reducing the potential differences that occur between the defibrillation electrode and the sensing electrode or the sensing electrodes in the critical application of the arrangement, i.e. the delivery of a defibrillation or shock pulse with high voltage. Finally, at least one embodiment of the invention is also based on the idea of attaining said substantial reduction by way of a switching unit for switching the sensing electrode, or each sensing electrode, to the potential of the defibrillation electrode in response to the output of a defibrillation shock.

At least one embodiment of the invention therefore makes it possible to create electrode leads for ICD or CRT-D arrangements having a substantially reduced diameter and less stiffness, and thereby contributes to the creation of ICT and CRT-D systems, the basic performance of which is therefore improved.

In one embodiment of the invention, the aforementioned switching unit for switching the sensing electrode(s) to the potential of the defibrillation electrode is disposed in the defibrillation device or the CRT-D device. In an alternative arrangement, the switching unit is disposed in the electrode lead, and, in fact, advantageously in the plug thereof.

In another embodiment, the switching unit comprises a switch element which functions automatically depending on the voltage. In particular, the switching unit comprises a varistor, such as a varistor composed of sintered ceramic of the SiC or ZnO type.

In another embodiment, the proposed arrangement is designed as a cardiac stimulation and defibrillation arrangement (CRT-D device), wherein the defibrillation device comprises a stimulation component, and the electrode lead comprises a stimulation electrode for transmitting stimulation pulses to cardiac tissue on the second electrode supply lead or with a third electrode supply lead, and the switching unit is designed to switch the stimulation electrode as well to the potential of the defibrillation electrode.

As noted above, an electrode lead which is suitable for use in the defibrillation arrangement described above is characterized in that the switching unit comprises a switching unit which functions automatically depending on the voltage. Especially in the embodiment as a CRT-D device comprising a stimulation electrode for delivering stimulation pulses to cardiac tissue with a third electrode supply lead, the latter is situated in the lead body with respect to the second electrode supply lead at a distance and with mutual insulation which are lower than the requirements for high-voltage resistance when typical defibrillation voltages are transmitted via the electrode lead.

Reference is made to the explanations above for further special embodiments of the electrode lead.

BRIEF DESCRIPTION OF THE DRAWINGS

Advantages and useful features of the invention will also become apparent from the descriptions that follow of embodiments with reference to the figures. In the figures.

DETAILED DESCRIPTION OF THE INVENTION

Figure 1:
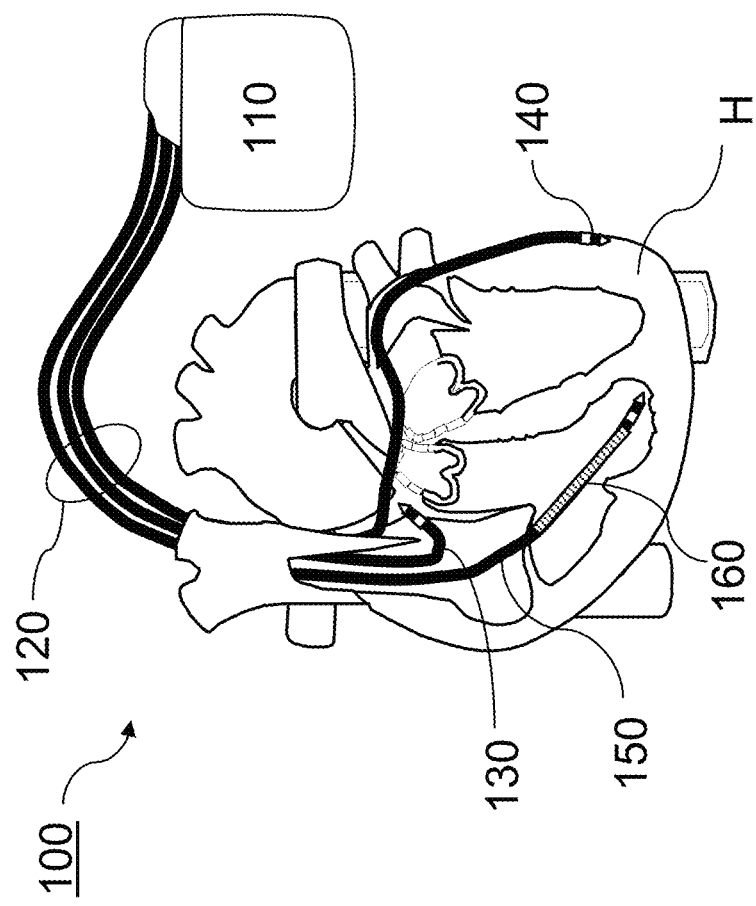
FIG. 1 shows a schematic depiction of a conventional cardiac stimulation and defibrillation arrangement.
Figure 2:
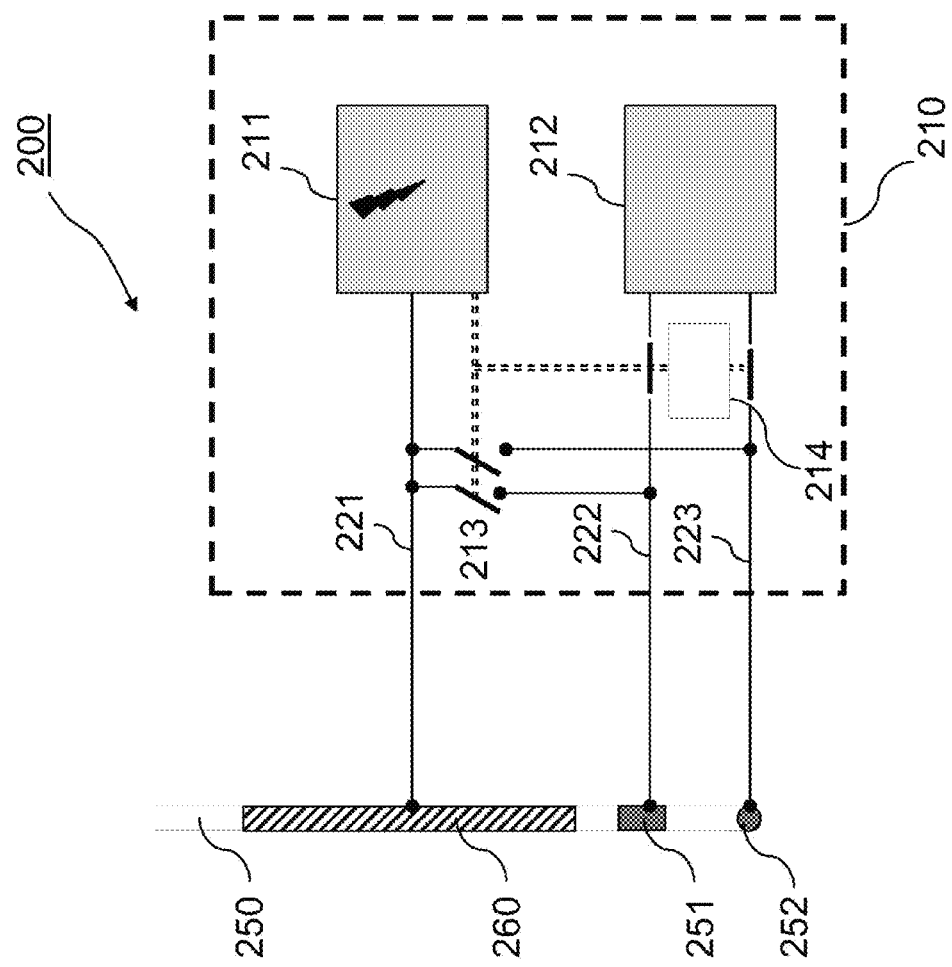
FIG. 2 shows a block diagram of an embodiment of the defibrillation arrangement according to the invention.

FIG. 2 shows a cardiac stimulation and defibrillation arrangement 200 formed of a stimulation and defibrillation device 210 and an electrode lead or electrode lead branch 250, wherein the design of the latter basically corresponds to that of lead branch 150 in the arrangement shown in FIG. 1. Electrode lead branch 250 is designed as a bipolar system for sensing cardiac action potentials and stimulating the ventricle, and comprises relevant electrodes 251 and 252. It also comprises a shock coil 260 as the defibrillation electrode. The counterelectrode for defibrillation is a housing (which is not depicted) of stimulation and defibrillation device 210. Device 210 comprises, in a manner known per se, a defibrillation component 211 and a sensing and stimulation component 212.

In order to be able to reduce the insulating clearances of electrode supply leads 222, 223 of sensing and stimulation electrodes 251, 252, and of supply lead 221 of shock electrode 260, a switching unit 213 is provided in addition to said device components, which switches sensing and stimulation electrodes 251, 252 to the potential of the defibrillation electrode 260 to deliver a defibrillation shock. A high-voltage protection switch 214, which is present anyway, of sensing and stimulation component 212 is used as the control unit for switching unit 213 in this case, and is controlled by defibrillation component 211 via a control signal and provides switching unit 213 with a suitable control potential.

Figure 3:
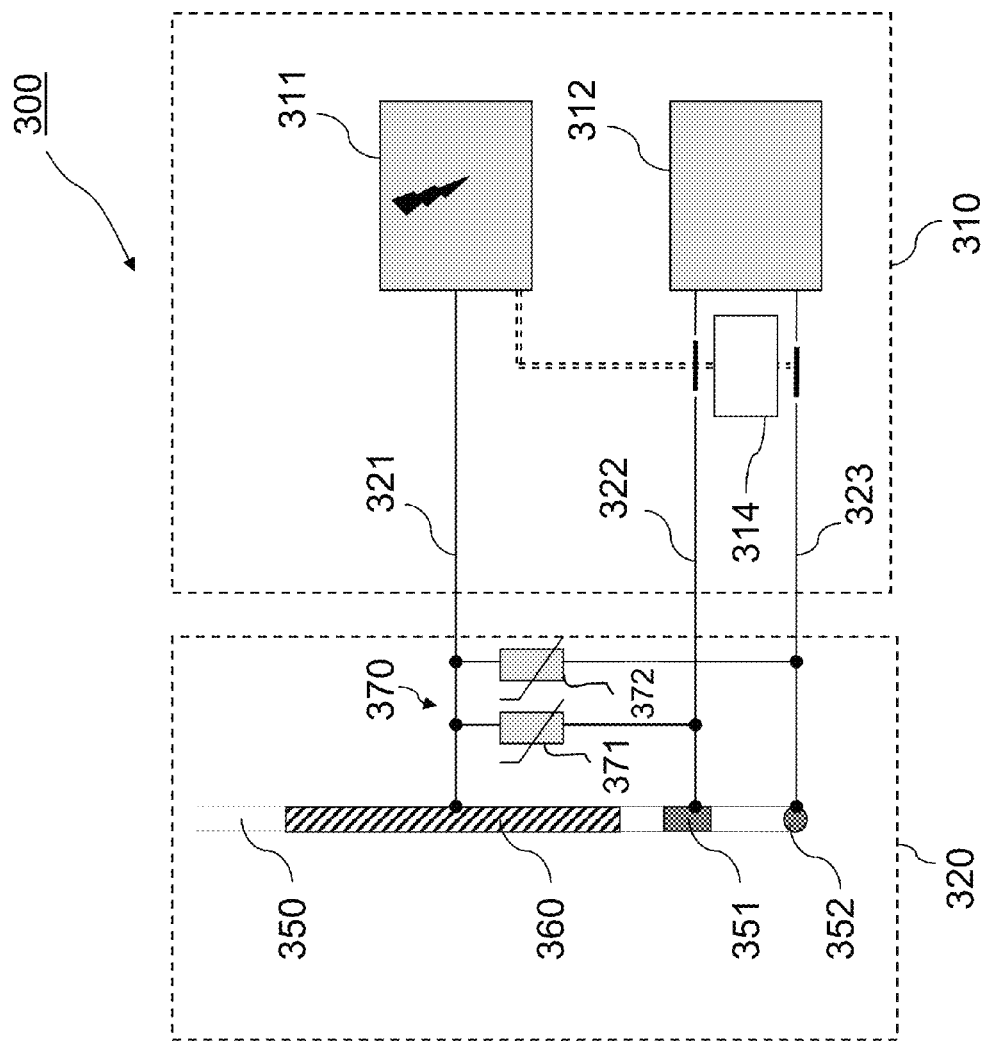
FIG. 3 shows a block diagram of another embodiment of the defibrillation arrangement according to the invention.

FIG. 3 shows a modified embodiment of this arrangement, wherein parts that are identical or perform a similar function are labeled with the same reference characters as in FIG. 2, and are not explained again here (i.e., electrode lead branch 350). The main difference from the arrangement shown in FIG. 2 is that the switching of the potential of sensing and stimulation electrodes 351, 352 to the potential of the defibrillation electrode 360 to deliver a defibrillation shock is carried out in this case using a switching unit 370 integrated in electrode lead 320, of cardiac stimulation and defibrillation arrangement 300, instead of via a component installed in the stimulation and defibrillation device 310.

In the embodiment shown, switching unit 370 which functions automatically (i.e. without a control signal from the CRT-D device) comprises two varistors 371, 372 connected between electrode supply lead 321, which connects defibrillation component 311 and defibrillation electrode 360, and one of the two other supply leads 322, 323, which connects sensing and stimulation component 312 to sensing and stimulation electrodes 351 and 352. Element 314 may be implemented as a high-voltage protection switch as may also be implemented as per FIG. 2 element 214.

Advantageously, the arrangement shown in FIG. 3 can also be formed of a stimulation and defibrillation device, which is known per se and is therefore not designed according to at least one embodiment of the invention, and a specially designed electrode lead, which contains the (automatically functioning) switch elements.

The embodiment of the invention is not limited to the above-described examples and emphasized aspects, but rather is possible in a large number of modifications that lie within the scope of handling by a person skilled in the art.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. An implantable defibrillation arrangement comprising
a stimulation and defibrillation device comprising
a housing,
a sensing and stimulation component within said housing, and
a defibrillation component within said housing;
an electrode lead coupled to said stimulation and defibrillation device, wherein said electrode lead comprises
a lead body;
an electrode lead plug coupled with said lead body;
a first electrode supply lead coupled with said electrode lead plug;
a second electrode supply lead coupled with said electrode lead plug;
a sensing electrode on said lead body configured to sense cardiac action potentials with the first electrode supply lead; and,
a defibrillation electrode on said lead body configured to transmit shock pulses to cardiac tissue with the second electrode supply lead; and,
a switching unit coupled with said sensing electrode and said defibrillation electrode and configured to switch the sensing electrode to a potential of the defibrillation electrode to deliver a defibrillation shock in response to an output of a defibrillation shock by the defibrillation component and to reduce insulation clearances of said first electrode supply lead and said second electrode supply lead;
wherein the switching unit comprises a switch element, which functions automatically dependent on voltage, wherein said switch element is connected between the first electrode supply lead and the second electrode supply lead, and,
wherein the switching unit is integrated in the electrode lead and disposed in the electrode lead plug; and,
wherein said stimulation and defibrillation device further comprises a high-voltage protection switch associated with said sensing and stimulation component,
wherein the high-voltage protection switch is configured to
control said switching unit as a control unit of the switching unit,
wherein said high-voltage protection switch is controlled by said defibrillation component via a control signal, and,
provide said switching unit with a suitable control potential to switch the sensing electrode to a potential of the defibrillation electrode to deliver the defibrillation shock in response to the output of the defibrillation shock by the defibrillation component.

2. The defibrillation arrangement according to claim 1, wherein the switch element comprises a varistor.

3. The defibrillation arrangement according to claim 1, wherein the electrode lead further comprises a stimulation electrode on said lead body configured to transmit stimulation pulses to the cardiac tissue on the second electrode supply lead or with a third electrode supply lead, and wherein the switching unit is further configured to switch the stimulation electrode as well to the potential of the defibrillation electrode.

4. The implantable defibrillation arrangement of claim 1, wherein the first and the second electrode supply leads are situated in the lead body with clearance and mutual insulation such that the first and second supply leads are resistant to high voltage, wherein said clearance and mutual insulation are configured to be lower than required for high-voltage resistance when typical defibrillation voltages are transmitted via the electrode lead.

5. The electrode lead according to claim 4, wherein the electrode lead further comprises a third electrode supply lead, and a stimulation electrode on the lead body configured to deliver stimulation pulses to cardiac tissue with the third electrode supply lead which is situated in the lead body with respect to the second electrode supply lead at a distance and with mutual insulation, such that the second and third electrode supply leads are resistant to high voltage, wherein said distance and said mutual insulation are configured to be lower than required for high-voltage resistance when typical defibrillation voltages are transmitted via the electrode lead.

6. The electrode lead according to claim 4, wherein the switching unit further comprises a second switch element, wherein the second switch element comprises a varistor, wherein the electrode lead further comprises a third electrode supply lead, and wherein the second switch element is connected between the second electrode supply lead and the first and third electrode supply leads.

7. An implantable defibrillation arrangement comprising
   a stimulation and defibrillation device comprising
      a housing,
      a sensing and stimulation component within said housing, and
      a defibrillation component within said housing;
   an electrode lead coupled to said stimulation and defibrillation device, wherein said electrode lead, wherein said electrode lead comprises
      a lead body;
      an electrode lead plug coupled with said lead body;
      a first electrode supply lead coupled with said electrode lead plug;
      a second electrode supply lead coupled with said electrode lead plug;
      a sensing electrode on said lead body configured to sense cardiac action potentials with the first electrode supply lead; and,
      a defibrillation electrode on said lead body configured to transmit shock pulses to cardiac tissue with the second electrode supply lead; and,
   a switching unit coupled with said sensing electrode and said defibrillation electrode and configured to switch the sensing electrode to a potential of the defibrillation electrode to deliver a defibrillation shock in response to an output of a defibrillation shock by the defibrillation component and to reduce insulation clearances of said first electrode supply lead and said second electrode supply lead;
      wherein the switching unit comprises a switch element, which functions automatically dependent on voltage, wherein said switch element is connected between the first electrode supply lead and the second electrode supply lead,
      wherein the switch element comprises a varistor, and,
      wherein the switching unit is integrated in the electrode lead and disposed in the electrode lead plug;
   wherein the electrode lead further comprises a stimulation electrode on the lead body configured to transmit stimulation pulses to the cardiac tissue on the second electrode supply lead or with a third electrode supply lead, and wherein the switching unit is further configured to switch the stimulation electrode as well to the potential of the defibrillation electrode; and, wherein said stimulation and defibrillation device further comprises a high-voltage protection switch associated with said sensing and stimulation component,
   wherein the high-voltage protection switch is configured to
      control said switching unit as a control unit of the switching unit,
         wherein said high-voltage protection switch is controlled by said defibrillation component via a control signal, and,
      provide said switching unit with a suitable control potential to switch the sensing electrode to a potential of the defibrillation electrode to deliver the defibrillation shock in response to the output of the defibrillation shock by the defibrillation component.

8. An implantable defibrillation arrangement comprising
   a stimulation and defibrillation device comprising
      a housing,
      a sensing and stimulation component within said housing, and
      a defibrillation component within said housing;
   an electrode lead coupled to said stimulation and defibrillation device, wherein said electrode lead, wherein said electrode lead comprises
      a lead body;
      an electrode lead plug coupled with said lead body;
      a first electrode supply lead coupled with said electrode lead plug;
      a second electrode supply lead coupled with said electrode lead plug;
      a third electrode supply lead;
      a sensing electrode on said lead body configured to sense cardiac action potentials with the first electrode supply lead; and,
      a defibrillation electrode on said lead body configured to transmit shock pulses to cardiac tissue with the second electrode supply lead; and,
   a switching unit coupled with said sensing electrode and said defibrillation electrode and configured to switch the sensing electrode to a potential of the defibrillation electrode to deliver a defibrillation shock in response to an output of a defibrillation shock by the defibrillation component and to reduce insulation clearances of said first electrode supply lead, said second electrode supply lead and said third electrode supply lead;
   wherein the switching unit comprises two switch elements, which function automatically dependent on voltage,
   wherein a first switch element of the two switch elements is connected between the first electrode supply lead and the second electrode supply lead, and a second switch element of the two switch elements is connected between the second electrode supply lead and the first and third electrode supply leads,
   wherein the switching unit is integrated in the electrode lead and disposed in the electrode lead plug, and
   wherein said stimulation and defibrillation device further comprises a high-voltage protection switch associated with said sensing and stimulation component, wherein the high-voltage protection switch configured to
      control said switching unit as a control unit of the switching unit,
         wherein said high-voltage protection switch is controlled by said defibrillation component via a control signal, and
      provide said switching unit with a suitable control potential to switch the sensing electrode to a potential of the defibrillation electrode to deliver the defibrillation shock in response to the output of the defibrillation shock by the defibrillation component.

9. The defibrillation arrangement according to claim 8, wherein the electrode lead further comprises a stimulation electrode on the lead body configured to transmit stimulation pulses to the cardiac tissue on the second electrode supply lead or with the third electrode supply lead, and wherein the switching unit is further configured to switch the stimulation electrode as well to the potential of the defibrillation electrode.

* * * * *